(12) United States Patent
Ding et al.

(10) Patent No.: US 10,509,031 B2
(45) Date of Patent: Dec. 17, 2019

(54) QUALITY/PROCESS CONTROL OF A LATERAL FLOW ASSAY DEVICE BASED ON FLOW MONITORING

(71) Applicant: Ortho-Clinical Diagnostics, Inc., Raritan, NJ (US)

(72) Inventors: Zhong Ding, Pittsford, NY (US); James E. Robinson, Rochester, NY (US); David A. Tomasso, Rochester, NY (US); David A. Heavner, Fairport, NY (US)

(73) Assignee: Ortho-Clinical Diagnostics, Inc., Raritan, NJ (US)

( * ) Notice: Subject to any disclaimer, the term of this patent is extended or adjusted under 35 U.S.C. 154(b) by 329 days.

(21) Appl. No.: 15/274,495

(22) Filed: Sep. 23, 2016

(65) Prior Publication Data
US 2017/0010262 A1 Jan. 12, 2017

Related U.S. Application Data

(62) Division of application No. 14/081,467, filed on Nov. 15, 2013, now Pat. No. 9,470,678.
(Continued)

(51) Int. Cl.
*G01N 33/53* (2006.01)
*G01N 33/558* (2006.01)
(Continued)

(52) U.S. Cl.
CPC .......... *G01N 33/558* (2013.01); *B01L 3/5023* (2013.01); *G01N 21/6428* (2013.01);
(Continued)

(58) Field of Classification Search
None
See application file for complete search history.

(56) References Cited

U.S. PATENT DOCUMENTS

| 5,120,643 A | 6/1992 | Ching et al. |
| 5,559,041 A | 9/1996 | Kang et al. |

(Continued)

FOREIGN PATENT DOCUMENTS

| CN | 1257204 A | 6/2000 |
| CN | 101779125 A | 7/2010 |

(Continued)

OTHER PUBLICATIONS

Chinese Office Action and Search Report for CN 201310574378.8; dated Jun. 30, 2017; 14 pgs.
(Continued)

*Primary Examiner* — Rebecca L Martinez
(74) *Attorney, Agent, or Firm* — K&L Gates LLP; Louis C. Cullman; Brian J. Novak

(57) ABSTRACT

A method for providing quality control on a lateral flow assay device or for triggering a process-related step, the device including a substrate having at least one sample receiving area, at least one reagent zone downstream and in fluid communication with the at least one sample receiving area, at least one detection zone downstream and in fluid communication with the at least one reagent zone and at least one wicking zone downstream of the at least one detection zone, each fluidly interconnected therewith along at least one fluid flow path. The detection material provided in the at least one reagent zone produces a detectable signal that can be tracked and monitored prior to the completion of at least one test being performed on the lateral flow assay device.

17 Claims, 7 Drawing Sheets

Related U.S. Application Data

(60) Provisional application No. 61/726,933, filed on Nov. 15, 2012.

(51) Int. Cl.
  *B01L 3/00* (2006.01)
  *G01N 21/64* (2006.01)
  *G01N 33/543* (2006.01)

(52) U.S. Cl.
  CPC ... *G01N 33/5302* (2013.01); *G01N 33/54366* (2013.01); *B01L 2200/143* (2013.01); *B01L 2300/0861* (2013.01); *B01L 2400/0406* (2013.01); *G01N 2021/6439* (2013.01)

(56) References Cited

U.S. PATENT DOCUMENTS

| | | | |
|---|---|---|---|
| 5,714,389 A | 2/1998 | Charlton et al. | |
| 5,989,921 A | 11/1999 | Charlton et al. | |
| 6,113,855 A | 9/2000 | Buechler | |
| 6,136,610 A | 10/2000 | Polito et al. | |
| 6,139,800 A | 10/2000 | Chandler | |
| 6,228,660 B1 | 5/2001 | May et al. | |
| 6,372,542 B1 | 4/2002 | Martin et al. | |
| 6,733,682 B1 | 5/2004 | Björkman et al. | |
| 6,811,736 B1 | 11/2004 | Öhman et al. | |
| 6,884,370 B2 | 4/2005 | Öhman et al. | |
| 7,416,700 B2 | 8/2008 | Buechler et al. | |
| 7,934,416 B2 | 5/2011 | Momose | |
| 8,025,854 B2 | 9/2011 | Öhman et al. | |
| 8,367,424 B2 | 2/2013 | Momose et al. | |
| 8,831,783 B2 | 9/2014 | Numajiri | |
| 9,097,665 B2 | 8/2015 | Wang et al. | |
| 2003/0044869 A1* | 3/2003 | Yeung | G01N 33/54306 435/7.92 |
| 2005/0042766 A1 | 2/2005 | Öhman et al. | |
| 2005/0220668 A1 | 10/2005 | Coville | |
| 2006/0239859 A1 | 10/2006 | Öhman et al. | 422/100 |
| 2006/0285996 A1 | 12/2006 | Öhman et al. | |
| 2006/0289787 A1 | 12/2006 | Öhman et al. | |
| 2007/0154970 A1* | 7/2007 | Buechler | G01N 33/53 435/7.92 |
| 2007/0231883 A1 | 10/2007 | Lindstrom et al. | |
| 2009/0162833 A1 | 6/2009 | Mertens et al. | |
| 2012/0040336 A1 | 2/2012 | Bisgrove et al. | |
| 2012/0122236 A1 | 5/2012 | Tarpey | |
| 2012/0258479 A1 | 10/2012 | Ding et al. | |
| 2014/0134653 A1 | 5/2014 | Ding et al. | |

FOREIGN PATENT DOCUMENTS

| | | |
|---|---|---|
| CN | 102323215 A | 1/2012 |
| EP | 1 947 457 B1 | 7/2011 |
| EP | 2 618 149 A1 | 7/2013 |
| EP | 2 618 150 A1 | 7/2013 |
| EP | 2 618 151 A1 | 7/2013 |
| EP | 2 781 920 A1 | 9/2014 |
| GB | 2 436 616 A | 10/2007 |
| JP | 2006-170654 | 6/2006 |
| JP | 2008-164360 | 7/2008 |
| JP | 2009-109429 | 5/2009 |
| JP | 2009-250710 | 10/2009 |
| JP | 2013-525762 | 6/2013 |
| WO | WO 95/09357 | 4/1995 |
| WO | WO 01/38873 A2 | 5/2001 |
| WO | WO 03/103835 A1 | 12/2003 |
| WO | WO 2005/089082 A2 | 9/2005 |
| WO | WO 2005/118139 A1 | 12/2005 |
| WO | WO 2006/013329 A1 | 2/2006 |
| WO | WO 2006/137785 A1 | 12/2006 |
| WO | WO 2007/149042 A1 | 12/2007 |
| WO | WO 2008/155579 A1 | 12/2008 |
| WO | WO 2009/125676 A1 | 10/2009 |
| WO | WO 2009/126735 A1 | 10/2009 |
| WO | WO 2009/145172 A1 | 12/2009 |
| WO | WO 2011/130625 A1 | 10/2011 |
| WO | WO 2014/078679 A1 | 5/2014 |

OTHER PUBLICATIONS

Japanese Office Action for JP 2013-235693; dated Sep. 26, 2017; 6 pgs.
Extended European Search Report for EP 17 163 375.3; dated May 26, 2017; 10 pgs.
Examination Report issued in related EP Application No. 17163375.3 dated Jun. 6, 2018.
Russian Office Action for RU 2013150854; dated Sep. 11, 2017; 10 pgs.
European Search Report for EP 13192854.1; dated Nov. 6, 2014; 6 pages.
U.S. Appl. No. 61/658,698, filed Jun. 12, 2012; Title: Lateral Flow Assay Devices for Use in Clinical Diagnostic Apparatus and Configuration of Clinical Diagnostic Apparatus for Same; 64 pages.

* cited by examiner

QUALITY/PROCESS CONTROL OF A LATERAL FLOW ASSAY DEVICE BASED ON FLOW MONITORING

CROSS-REFERENCE TO RELATED APPLICATION

This patent application is a divisional application of, and claims priority and benefit to, co-pending U.S. patent application Ser. No. 14/081,467, filed Nov. 15, 2013 and entitled "Quality/Process Control of a Lateral Flow Assay Device Based on Flow Monitoring", which is a non-provisional application of U.S. provisional patent application Ser. No. 61/726,933, filed Nov. 15, 2012 and entitled "Quality/Process Control of a Lateral Flow Assay Device Based on Flow Monitoring". All of the aforementioned patent(s) and patent application(s) are herein incorporated by reference in their entirety.

TECHNICAL FIELD

This application relates to the field of clinical diagnostics and more specifically to in-situ monitoring of a lateral flow assay device for purposes of quality and process control. According to one version, readings using a detection instrument can be taken at various portions of a lateral flow assay device prior to completion of at least one test in order to assess whether or not certain key processes have worked within anticipated and prescribed limits. According to another version, readings using a detection instrument can be used to trigger various process-related events.

BACKGROUND

Diagnostic assays are widespread and central for the diagnosis, treatment and management of many diseases. In that regard, different types of diagnostic assays have been developed over the years in order to simplify the detection of various analytes in clinical samples such as blood, serum, plasma, urine, saliva, tissue biopsies, stool, sputum, skin or throat swabs and tissue samples or processed tissue samples. These assays are frequently expected to provide a fast and reliable result, while being easy to use and inexpensive to manufacture.

One common type of disposable assay device includes a zone or area for receiving the liquid sample, at least one reagent zone, and a reaction zone also known as a detection zone. These assay devices, commonly known as lateral test strips, employ a porous material, e.g., nitrocellulose, defining a path for fluid capable of supporting capillary flow. Examples include those devices shown in U.S. Pat. Nos. 5,559,041, 5,714,389, 5,120,643, and 6,228,660, all of which are incorporated herein by reference in their entireties.

The sample-receiving zone of these assay devices frequently consists of a more porous material, capable of absorbing the liquid sample, and, when separation of blood cells is required, also effective to trap the red blood cells. Examples of such materials are fibrous materials, such as paper, fleece, gel, or tissue, comprising e.g., cellulose, wool, glass fiber, asbestos, synthetic fibers, polymers, or mixtures of the same.

Another type of lateral flow assay device is defined by a non-porous substrate having a plurality of upwardly extending projections configured to induce capillary flow. Examples of such devices are disclosed in U.S. Pat. No. 8,025,854B2, WO 2003/103835, WO 2005/089082, WO2005/118139 and WO 2006/137785, all of which are incorporated by reference herein in their entireties.

A known non-porous assay device of the above type is shown in FIG. 1. The assay device 1 has at least one sample addition zone 2, a reagent zone 3, at least one detection zone 4, and at least one wicking zone 5, each disposed on a common substrate. These zones are aligned along a defined flow path by which sample flows from the sample addition zone 2 to the wicking zone 5. Capture elements, such as antibodies, are supported in the detection zone 4, these elements being capable of binding to an analyte of interest, the capture elements being optionally deposited on the device (such as by coating). In addition, a labeled conjugate material, also capable of participating in reactions that will enable determination of the concentration of the analyte, is separately deposited on the device in the reagent zone, wherein the conjugate material carries a label for detection in the detection zone of the assay device.

The conjugate material is gradually dissolved as the sample flows through the reagent zone, forming a conjugate plume of dissolved labeled conjugate material and sample that flows downstream along the defined flow path of the device to the detection zone. As the conjugate plume flows into the detection zone, the conjugated material will be captured by the capture elements such as via a complex of conjugated material and analyte (e.g., as in a "sandwich" assay) or directly (e.g., as in a "competitive" assay). Unbound dissolved conjugate material will be swept past the detection zone 4 and into the wicking zone 5.

An instrument such as that disclosed in US 2006/0289787A1, US 2007/0231883A1, U.S. Pat. Nos. 7,416,700 and 6,139,800, all incorporated by reference in their entireties herein, is configured to detect the bound conjugated material in the detection zone. Common labels include fluorescent dyes that can be detected by instruments which excite the fluorescent dyes and incorporate a detector capable of detecting the resulting fluorescence.

In the foregoing devices and in the conduction of assays, the resulting level of signal in the detection zone is read using a suitable detection instrument after the conjugate material has all been dissolved and sample and unbound conjugate material and wash fluid added to a reagent zone of the device has reached and subsequently filled the wicking zone of the device.

Issues may develop using the above stated devices in advance of the completion of the test, for example, due to manufacturing or other defects, which delay, retard or immobilize the movement of fluid in the lateral flow assay device. To that end, it would be beneficial to determine the presence of such error conditions proactively. In addition, there is a general need in the field to improve the efficiency and efficacy of lateral flow assay devices, such as those described above, for example, to determine latent errors in the device or in process flow prior to analyte testing.

In addition, the lateral flow assay device may require external operations such as, for example, the introduction of wash fluid or other reagents, as noted above. It would be beneficial to provide process-related triggers to optimally indicate when this fluid when or should be added.

SUMMARY OF THE INVENTION

Therefore and according to one aspect, there is provided a method for providing quality control upon a lateral flow assay device. The lateral flow assay device comprises a substrate having a plurality of discrete zones including at least one sample addition zone. At least one detection zone is disposed downstream of the at least one sample addition zone and at least one wicking zone downstream of the at least one detection zone, each of the zones being fluidly interconnected along a fluid flow path through which sample flows under capillary action from the sample addition zone to the wicking zone. The method comprises the steps of: adding sample to the sample addition zone before, during or after installation; combining sample and reagent, wherein the sample and reagent may be combined prior to the adding of sample to the sample addition zone or on the assay device, said reagent including at least one detection material that produces a detectable signal; making at least one time-related measurement relating to the presence of the detectable signal in the lateral flow assay device after sample is added to the sample addition zone; and comparing the at least one time-related measurement to a predetermined threshold to determine whether the device is operating properly.

In one version, the assay device includes at least one reagent zone disposed downstream of the sample addition zone, the reagent zone containing the at least one detection material.

In one version, the method can further include the step of diverting a portion of sample from the flow path of the lateral flow device to enable detection or lack of detection of the detectable signal by a detection instrument. According to one embodiment, the detection material produces a fluorescent signal that can be detected by a fluorimeter or similar instrument. According to one embodiment, the diverting step can include the step of providing at least one capillary channel, the at least one capillary channel extending from the flow path and further extending through a linear detection path of the lateral flow assay device aligned with the detection instrument.

The linear detection path of the assay device can extend along a linear portion of said flow path that includes the at least one detection zone wherein the at least one capillary channel extends from the wicking zone. In one embodiment, the at least one capillary channel includes an enlarged intermediate portion forming a read window aligned with the detection zone. Preferably, the at least one capillary channel is vented and is configured to divert sample from a portion of the flow path prior to the at least one detection zone. In one version, the at least one capillary channel extends from at least one of the entrance and exit of the wicking zone.

The method can include the additional steps of monitoring at least one detection zone of the device; determining the time period that sample carrying the detectable signal is first detected relative to the at least one detection zone, wherein said time period is initiated at the sample adding step; and comparing the measured time period with a known time period to ascertain whether the lateral flow device is operating properly.

Still further, the method can include the additional steps of installing the lateral flow assay device into a testing apparatus in advance of testing the device and in which sample is initially not present in the testing apparatus; and monitoring the device with a detection instrument to determine whether the detectable signal is present in predetermined portions of the lateral flow assay device.

According to at least one other version, the method can include the additional steps of determining the time that sample carrying the detectable signal has initially flowed into a predetermined portion of the wicking zone; and comparing the determined time to a known time period to ascertain whether the device is operating properly.

In one version, the method can include the additional steps of determining the time that the sample carrying the detectable signal has flowed between at least two portions of the device; and comparing the time against a predetermined threshold. In one embodiment, at least one of the at least two portions or each of the at least two portions are in the wicking zone of the lateral flow assay device. In one version, the least two portions include the entrance and exit of the wicking zone.

According to at least one version, the detection instrument is used for determining the presence of at least one analyte in at least one detection zone once sample has fully flowed through the lateral flow device, and in which the method further comprises the additional steps of: monitoring at least one portion of the lateral flow assay device; determining the time period in which the detection material in the at least one reagent zone has fully dissolved based on the monitoring step; and comparing the determined time period to a known time period.

In one preferred version, analyte detection does not occur unless the determined time period successfully compares to the known time period.

In another version, the method can further include the steps of: making a plurality of time-based measurements at least one predetermined portion of the device; and creating a time history of the detectable signal based on the measurements. An error notification can be provided if the determined time is not favorably compared within the predetermined time period.

According to another aspect, there is provided a method for providing quality control upon a lateral flow assay device. The device comprises a substrate having a plurality of discrete zones including at least one sample addition zone. At least one detection zone is disposed downstream of the at least one sample addition zone and at least one wicking zone downstream of the at least one detection zone, each of the zones being fluidly interconnected along a fluid flow path through which sample flows under capillary action from the sample addition zone to the wicking zone. The method comprises the steps of: installing the lateral flow assay device into a testing apparatus in advance of testing the device and in which sample is initially not present in the testing apparatus; combining sample and a reagent, wherein the sample and reagent may be combined prior to the adding of sample to the sample addition zone or on the assay device, said reagent including at least one detection material that produces a detectable signal; and monitoring the device with a detection instrument to determine whether the detectable signal is present in predetermined portions of the lateral flow assay device.

According to yet another version, there is provided a lateral flow assay device comprising: a substrate having at least one sample receiving zone and in fluidic communication therewith. The device further comprises at least one detection zone downstream of and fluidly connected with the at least one sample addition zone, the at least one detection zone being disposed along a detection or scan path that enables a detection instrument to determine the presence of at least one analyte of interest in the at least one detection zone. A wicking zone is disposed downstream of the at least one detection zone, each of the zones being fluidly interconnected to form a flow path in which sample flows under capillary action from the sample receiving zone to the wicking zone and in which sample is combined with a reagent, said reagent including at least one detection material that produces a detectable signal; and at least one capillary channel for diverting a portion of sample. The at least one capillary channel extends from a portion of the flow path and further extends through the linear detection path of the device to permit in situ detection thereof.

In one version, the device includes at least two capillary channels. In one embodiment, the at least two capillary channels are arranged relative to disparate portions of the wicking zone. The at least one capillary channel can include an enlarged intermediate portion aligned with the detection path and acting as a read window for a detection instrument. According to one version, the at least one capillary channel is vented and diverts sample from a portion of the flow path in advance of the at least one detection zone. The device can further include least one wash or additional reagent zone disposed along the flow path.

According to yet another aspect, a method is provided for processing a lateral flow assay device, the lateral assay device comprising a substrate having at least one sample addition zone. At least one detection zone is disposed downstream of the at least one sample addition zone and at least one wicking zone disposed downstream of the at least one detection zone, each of said zones being fluidly connected along a flow path in which sample flows from the sample addition zone to the wicking zone and in which the method comprises the steps of: adding a quantity of a sample to the sample receiving zone of the lateral flow assay device; combining sample and a reagent, wherein the sample and reagent can be combined prior to the adding of sample to the sample addition zone or on the assay device, said reagent including at least one detection material that produces a detectable signal; and triggering a process-related event based upon the detection of the detectable signal in at least one area of the lateral flow device.

According to one version, the assay device includes at least one reagent zone disposed downstream of the sample addition zone that includes the reagent having the detection material.

In one version, the method can include the additional steps of: monitoring at least one zone of the lateral flow device downstream of the reagent zone(s); determining the time sample carrying the detectable signal is initially detected in said at least one zone; comparing the determined time to a known time period; and triggering the process-related event upon said lateral flow device only if said determined time is within a threshold of said known time period.

In one embodiment, the process-related event is the dispensing of at least one wash fluid onto a wash area of the lateral flow assay device to flush out sample and detection material and in which detection takes place in a predetermined portion of the wicking zone of the lateral flow device.

In at least one version, the method includes the additional steps of providing at least one capillary channel for diverting a portion of sample from the flow path across a linear detection path of the lateral flow assay device extending through the at least one detection zone; and detecting the presence or lack of presence of the detectable signal in said channel, the detecting step causing the triggering of the process-related event. The detection or scan path is preferably, but not necessarily, linear.

In one version, the detectable signal is optically detectable. More specifically, and in at least one embodiment the detectable signal is fluorescent. Even more specifically, the detection material can be a conjugate material that produces a fluorescent plume.

The lateral flow assay device can include a plurality of projections disposed on at least one zone, the plurality of projections being dimensioned to induce capillary flow along the flow path.

The method can include the additional step of monitoring at least one predetermined zone of the assay device for the presence of detection material in any zone outside of the at least one reagent zone and prior to application of sample to the sample addition zone. At least one flow related parameter can be calculated based on the monitoring of at least one of the appearance and cessation of the detectable signal at one or more than one predetermined portion of the lateral flow device, such as the wicking zone.

The lateral flow device can be installed into a testing apparatus, the testing apparatus including a detection instrument capable of detecting the detectable signal. In one version, the testing apparatus is a clinical analyzer, such as bench, table-top or main frame analyzer. In another version, the testing apparatus is a point of care device.

The method can include the additional step of monitoring the at least one area of the lateral flow device downstream of the reagent zone and determining the amount of dissolved detection material in the area over a time period.

Preferably, the detection of the termination of a fluorescent plume or other detection signal should occur within a prescribed period of elapsed time following the first appearance of the signal. In the instance in which the lateral flow assay device includes a plural number (N) of reagent zones, there may be some variation in the elapsed time to complete dissolution for each of the reagent zones, and therefore the resulting signal that is detected by a suitable detection instrument may be in a stepped format. If these steps occur over an excessive period of time, there may be reason to believe that the dissolution has not occurred in a normal fashion, thereby resulting in an error condition indicative of excessively slow fluid flow rate through the device, an inadequate sample volume, excessive detection material initially present in the lateral flow device or other defect in the reagent zone causing dissolution to occur too slowly. Conversely and if the end of the fluorescent plume or other perceivable detection signal is detected at some time prior to the minimum elapsed time, this may indicate an excessive fluid flow rate, the lack of sufficient detection material in the lateral flow device or other defect involving the at least one reagent zone that caused dissolution to occur too quickly.

According to another aspect various flow-related parameters, such as flow velocity or fluid flow rate, can be calculated based upon the appearance of the detection signal at any two points within the assay device, such as, for example, within the wicking zone thereof. For example, flow velocity can be utilized to provide post prediction corrections. In one version and if the wicking zone is not in the linear scan path of the assay device relative to a fixed detection instrument, at least one capillary channel can be brought out from one or more points in the wicking zone or other portion of the flow path to a position disposed along the scan path of the testing apparatus in order to enable signal detection by the detection instrument.

According to one version, the position of the flow front in the wicking zone of the device could be monitored by the detection instrument, wherein this position could act as a trigger point for the start of the wash event. In addition, wash can be used for background removal.

According to yet another version and if the detection signal is monitored at known positions of the assay device on a periodic/frequent basis, a time history of the dissolution of the detection material can be obtained and charted. The area under the resulting plotted curve (possibly compensated with the fluid flow rate) could further provide a potential means for detecting a shortage or excess of detection material being present in the device with possible causes being attributable to manufacturing defects in or damage to the lateral flow device, among other potential causes.

Moreover and according to yet another aspect, the presence of unconjugated detection material in specific areas of the assay device, such as the wicking area, can also be detected. In the latter instance and in which the wicking zone is not part of the detection or scan path of the device, at least one capillary channel could be branched out from the wicking zone at the point of interest and brought up to the flow path where the presence of this material could be detected. In one specific version and during deposition of materials during manufacture of the assay device, a droplet of unconjugated fluorophore could be spotted in the capillary just beyond where the channel joins the wicking zone. This material would be easily dissolved by the fluid entering the capillary and would provide a robust signal when the fluid arrives at the end of the capillary (which is aligned with the linear scan path of the device). Similarly and if it was important to track the location of the fluid front as it progresses along the flow channel of the device, a very small amount of unconjugated fluorophore could be deposited at the entrance of the flow channel in that conjugate material has not had adequate time to dissolve in this initial front of fluid.

According to another version, a so called "dry" scan of the lateral flow assay device could also be performed using a suitable detection instrument and in which information obtained from this latter scan could be processed to determine defects in the device or detection of debris that has a fluorescent signal that could affect actual sample results or indicate the device has been previously used.

A suitable detection instrument used in accordance with the herein described method can include several forms. For example, one version could be based upon a scanning apparatus, such as a fluorimeter, or alternatively upon an imaging apparatus and image analysis to determine, for example, the presence and position of at least one fluorescent fluid front of a lateral flow assay device. According to yet another alternative version, infrared sensors could also be utilized in order to track the position of fluid position in the lateral flow assay device. For instance, an infrared sensor could be used to sense the ~1200 nanometer peak that is associated with water in the fluid sample to verify that sample had indeed touched off onto the substrate of the lateral flow assay device. It will be readily apparent that other alternative detection approaches could be utilized herein.

A significant advantage borne from the herein described method is that quality control and or triggering of process-related events occur using the same detection material that detects or quantifies analyte concentration required in terms of the assay device, thereby permitting the overall testing process to be more robustly and effectively managed.

Another advantage realized by the presently disclosed method is that potential error conditions relating to lateral flow assay devices can be easily determined in a proactive manner and prior to the time typically required for the completion of a test(s).

Another advantage is that flow and flow-related characteristics of a lateral flow assay device can be easily calculated.

Yet still another advantage is that the herein described method can be performed without significant device modification and using existing scanning or other detection instrumentation.

It will be readily apparent that other variations and modifications are possible in accordance with the following Detailed Description, which should be read in conjunction with the accompanying drawings.

DETAILED DESCRIPTION

Figure 1:
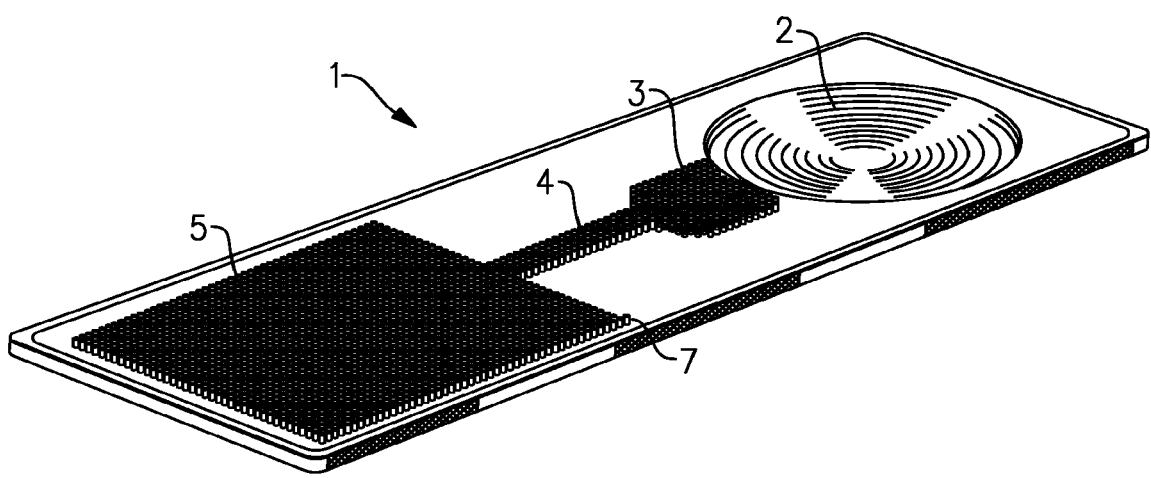
FIG. 1 is a plan view of a known lateral flow assay device.

The following description relates to certain embodiments for monitoring lateral flow assay devices in advance of completion of a test(s) on the device. It will be readily apparent that the embodiments described herein are intended to be exemplary and therefore numerous other variations and modifications are possible. In addition, several terms are used throughout the following discussion for purposes of providing a suitable frame of reference in regard to the accompanying drawings. To that end, these terms should not be regarded as being overly restrictive in terms of the scope of the described apparatus and methods, unless otherwise specifically indicated herein.

It should further be noted that the accompanying drawings are not necessarily presented to scale and therefore no narrowing interpretation should be made in terms of dimensions that have been depicted.

As used in this specification and the appended claims, the singular forms "a", "an" and "the" are intended to further include plural referents unless the context clearly dictates otherwise.

The term "about" as used in connection with a numerical value throughout the description and the claims denotes an interval of accuracy, familiar and acceptable to a person skilled in the art. The interval governing this term is preferably ±10%.

In terms of defining certain of the terms that follow, the term "analyte" is used as a synonym of the term "marker" and intended to minimally encompass any chemical or biological substance that is measured quantitatively or qualitatively and can include small molecules, proteins, antibodies, DNA, RNA, nucleic acids, virus components or intact viruses, bacteria components or intact bacteria, cellular components or intact cells and complexes and derivatives thereof.

The term "sample" herein means a volume of a liquid, solution or suspension, intended to be subjected to qualitative or quantitative determination of any of its properties, such as the presence or absence of a component, the concentration of a component, etc. Typical samples in the context of the present invention as described herein are human or animal bodily fluids such as blood, plasma, serum, lymph, urine, saliva, semen, amniotic fluid, gastric fluid, phlegm, sputum, mucus, tears, stool, etc. Other types of samples are derived from human or animal tissue samples where the tissue sample has been processed into a liquid, solution, or suspension to reveal particular tissue components for examination. The embodiments of the present invention are applicable to all bodily samples, but preferably to samples of whole blood, urine or sputum.

In other instances, the sample can be related to food testing, environmental testing, bio-threat or bio-hazard testing, etc. This represents only a small example of samples that can be used in the present invention.

In the present invention, the determination based on lateral flow of a sample and the interaction of components present in the sample with reagents present in the device or added to the device during the procedure and detection of such interaction, either quantitatively or qualitatively, may be for any purpose, such as diagnostic purposes. Such tests are often referred to as lateral flow assays.

Examples of diagnostic determinations include, but are not limited to, the determination of analytes, also called markers, specific for different disorders, e.g., chronic metabolic disorders, such as blood glucose, blood ketones, urine glucose (diabetes), blood cholesterol (athereosclerosis, obesitas, etc.); markers of other specific diseases., e.g., acute diseases, such as coronary infarct markers (e.g., tropinin-T, NT-ProBNP), markers of thyroid function (e.g., determination of thyroid stimulating hormone (TSH)), markers of viral infections (the use of lateral flow immunoassays for the detection of specific viral antibodies), etc.

Yet another important field is the field of companion diagnostics in which a therapeutic agent, such as a drug, is administered to an individual in need of such a drug. An appropriate assay is then conducted to determine the level of an appropriate marker to determine whether the drug is having its desired effect. Alternatively, the assay device usable with the present invention can be used prior to administration of a therapeutic agent to determine if the agent will help the individual in need.

Yet another important field is that of drug tests, for easy and rapid detection of drugs and drug metabolites indicating drug abuse; such as the determination of specific drugs and drug metabolites in a urine or other sample.

The term "lateral flow assay device", as discussed herein refers to any device that receives fluid, such as sample, and includes a laterally disposed fluid transport or flow path along which various stations or sites (zones) are provided for supporting various reagents, filters and the like through which sample traverses under the influence of capillary or other applied forces and in which lateral flow assays are conducted for the detection of at least one analyte of interest.

The terms "automated clinical analyzer", "clinical diagnostic apparatus" or "clinical analyzer" as discussed herein, refer to any apparatus enabling the scheduling and processing of various analytical test elements, including lateral flow assay devices, as discussed herein and in which a plurality of test elements can be initially loaded for processing. This apparatus further includes a plurality of components/systems configured for loading, incubating and testing/evaluating a plurality of analytical test elements in automated or semi-automated fashion and in which test elements are automatically dispensed from at least one contained storage supply, such as a cartridge, without user intervention.

The term "testing apparatus" refers to any device or analytical system that enables the support, scheduling and processing of lateral flow assay devices. A testing apparatus can include an automated clinical analyzer or clinical diagnostic apparatus such as a bench, table-top or main frame clinical analyzer, as well as point of care and other suitable devices. For purposes of this definition, the testing apparatus may include a plurality of components/systems for loading and testing/evaluating of at least one lateral flow assay device including detection instruments for detecting the presence of at least one detectable signal of the assay device.

The terms "zone", "area" and "site" are used in the context of this description, examples and claims to define parts of the fluid flow path on a substrate, either in prior art devices or in at least one lateral flow assay device according to an embodiment of the invention.

The term "reaction" is used to define any reaction, which takes place between components of a sample and at least one reagent or reagents on or in the substrate, or between two or more components present in the sample. The term "reaction" is in particular used to define the reaction, taking place between an analyte and a reagent as part of the qualitative or quantitative determination of the analyte.

The terms "substrate" or "support" refers to the carrier or matrix to which a sample is added, and on or in which the determination is performed, or where the reaction between analyte and reagent takes place.

The term "detection" and "detection signal" refers herein to the ability to provide a perceivable indicator that can be monitored either visually and/or by machine vision such as a detection instrument.

The term "process-related event" refers herein to an event that occurs prior to the detection of analyte in a lateral flow assay device, such as, for example, the addition of at least one reagent, such as a wash reagent.

Figure 2:
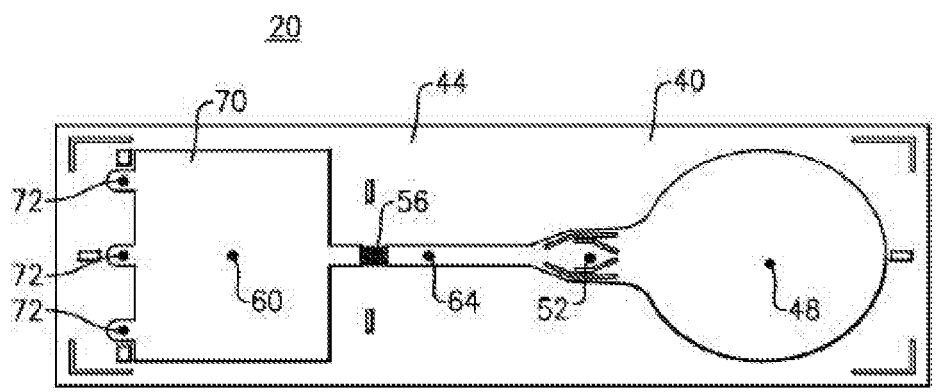
FIG. 2 is a plan view of another lateral flow assay device.

Referring to FIG. 2, there is shown one version of a lateral flow assay device 20, the device including a planar substrate 40 which can be made from a moldable plastic or other suitable non-porous material. The substrate 40 is defined a top surface 44, which is further defined by a plurality of discrete areas or zones including a sample receiving zone 48, a reagent zone 52, a plurality of detection zones 56 (one shown) and a receiving or wicking zone 60. According to this design, each of the above-noted zones are fluidly interconnected with one another in linear fashion along a flow channel 64 and in which a plurality of projections, similar to those provided in the device 1, FIG. 1, are disposed within at least one of the zones and/or the flow channel, the projections extending upwardly from either the lower surface of the flow channel 64 or the discrete zones defined on the assay device 20.

The projections are preferably dimensioned to induce lateral capillary flow, wherein the projections preferably include a height, diameter and/or center to center spacing to induce flow. In one version thereof, the projections can be sufficiently dimensioned so as to spontaneously induce capillary flow without the need for additional structure (i.e., side walls, cover or lid) or the application of any externally applied forces. According to this design, a defined fluid flow path is created from the sample addition zone 48 extending to the wicking zone 60 that is at least partially open. In another embodiment, the flow path is entirely open. By "open" what is meant is that there is no lid or cover which is maintained at a distance that would contribute to capillary flow. Thus a lid, if present as physical protection for the flow path and the device, does not contribute to the capillary flow in the flow path. According to this specific design, a hydrophilic foil layer 70 is applied to the top of the projections in the wicking zone 60 in order to increase fluid flow in the device and in which a plurality of vents 72 are defined in the foil layer. An open lateral flow path is described including he defined projections, for example, in the following published applications: WO 2003/103835, WO 2005/089082; WO 2005/118139; WO 2006/137785; and WO 2007/149042, all of which are incorporated by reference in their entireties. The extending projections have a height (H), diameter (D) and a distance or distances between the projections (t1, t2) such, that lateral capillary flow of an applied fluid, such as plasma, preferably human plasma, in the zone is achieved. These relationships are discussed in US 2006/0285996, which is incorporated by reference in its entirety.

In addition to optimizing the above-mentioned height, diameter and a distance or distances, the above-noted projections may be given a desired chemical, biological or physical functionality, e.g. by modifying the surface of the projections for purposes, for example, of the reagent zone(s) and detection zone(s) of the assay device 20. In one embodiment, the projections have a height in the interval of about 15 to about 150 µm, preferably about 30 to about 100 µm, a diameter of about 10 to about 160 µm, preferably 40 to about 100 µm, and a gap or gaps between the projections of about 3 to about 200 µm, preferably 5 to 50 µm or 10 to about 50 µm from each other. The flow channel 64 between the sample addition zone 48 and the wicking zone 60 may have a length of about 5 to about 500 mm, preferably about 10 to about 100 mm, and a width of about 0.3 to about 10 mm, preferably about 0.3 to about 3 mm, preferably about 0.5 to 1.5, and preferably about 0.5 to 1.2 mm. The projections, according to this device design, are substantially cylindrical in terms of their configuration and cross section. However, their specific design of the projections can also easily be varied to those of different shapes (e.g., rhombic, hexagonal, etc) and sizes to augment flow, as well as to filter materials.

In another embodiment, the flow path is porous and includes a porous material, e.g., nitrocellulose, defining the flow path capable of supporting capillary flow. Examples include those shown in U.S. Pat. Nos. 5,559,041, 5,714,389, 5,120,643, and 6,228,660, all of which are incorporated herein by their entireties.

Figure 3:
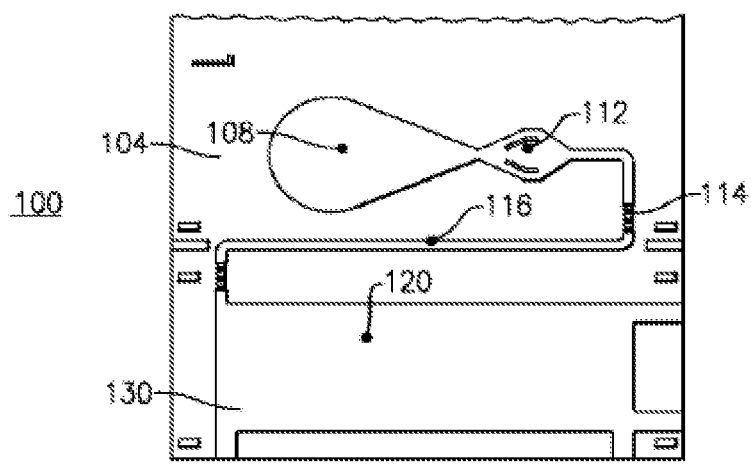
FIG. 3 is a plan view of another lateral flow assay device.

Referring to FIG. 3, there is depicted another lateral flow assay device 100 which is defined by a planar substrate 104 which can be made from a moldable plastic or other suitable non-porous material and having a sample addition zone 108 disposed at one end of a lateral folded fluid flow path extending through a reagent zone 112 containing a detection material, such as a conjugate or other reagent that further extends to at least one detection zone 114 disposed along a flow channel 116 of the device 100, the latter further extending to a wicking zone 120 that defines the opposite end of the lateral fluid flow path. According to this particular configuration, two distinct folds are present, a first fold between the reagent zone 112 and a first or entry end of the detection zone 114 and a second fold between a second or exit end of the detection zone and the wicking zone 120. The folded configuration described is exemplary and other suitable flow path options are easily configurable. In addition and optionally, the lateral fluid flow path may further include additional separate zones containing reagents, such as detection conjugate, as well other zones, areas or sites along this path that can be utilized used for addition of other reagents, such as for example, washing of dispensed sample and any bound or unbound components thereof.

According to this particular embodiment, a plurality of projections 130, similar to those previously depicted in FIG. 1, extend upwardly from the top surface of the substrate 104 substantially defining the active zones defined within the bordering line of this device 100 wherein the projections are specifically designed dimensionally in terms of their height and diameters, as well as with relative interpillar spacings, so as to solely promote spontaneous lateral capillary flow along the defined fluid flow path between the sample addition zone 108 and the wicking zone 120. As discussed infra, this specific device design is referred to as an "open" system or device, meaning that side walls and a cover are not necessarily required to assist in the creation of capillary force and as described in the following published applications: WO 2003/103835, WO 2005/089082; WO 2005/118139; WO 2006/137785; and WO 2007/149042, previously incorporated by reference in their entireties. It will further be noted that a cover or lid can be optionally included; for example, a cover (not shown) can be added to the device as needed, the cover being spaced in relation to the projections so as not contribute to the lateral capillary flow of a sample liquid. It is has been determined, however, similar to that depicted in FIG. 1, that the addition of a hydrophilic foil or layer directly onto at least a portion of the wicking area 120 alone does contribute to the overall flow rate (process time) of an aspirated sample.

In another embodiment, the flow path of the assay device is porous and includes a porous material, e.g., nitrocellulose, defining the flow path capable of supporting capillary flow. Examples include those shown in U.S. Pat. Nos. 5,559,041, 5,714,389, 5,120,643, and 6,228,660, all of which have been incorporated herein by their entireties.

Figure 4:
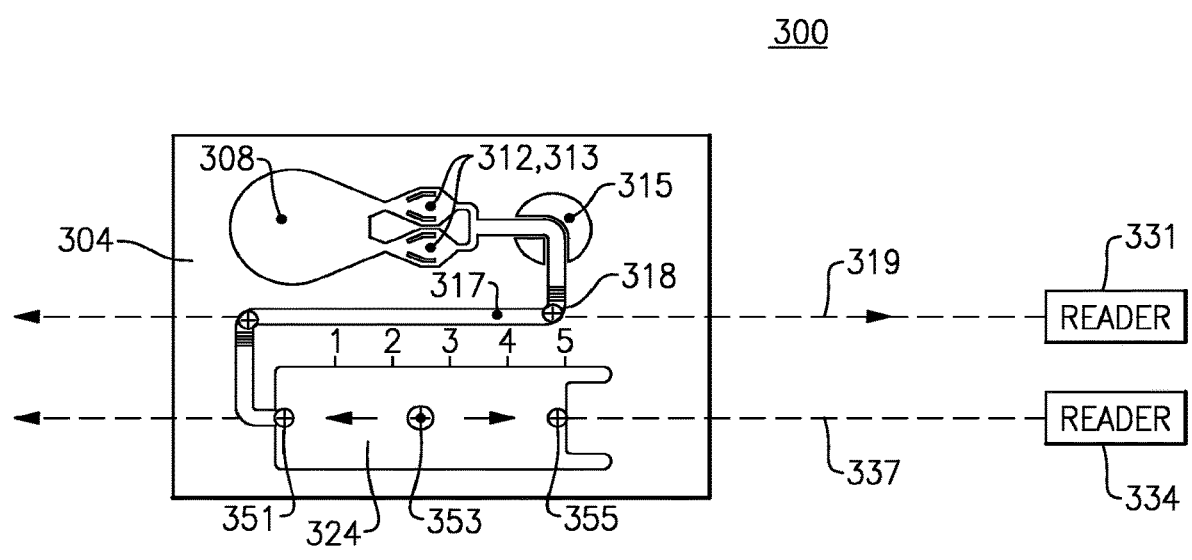
FIG. 4 is a plan view of yet another version of a lateral flow assay device, each of the depicted devices being useful for purposes of the methods described herein.

An exemplary design of yet another lateral flow assay device 300, which is herein described for purposes of the present invention, is depicted in FIG. 4. Though this particular assay device is referred to throughout the remainder of this description in terms of an exemplary embodiment, it will be readily apparent that other device designs and possible variants of these designs could also be similarly configured. The exemplary assay device 300 is defined by a substrate 304 including a liquid sample addition zone 308 that receives sample from a liquid dispenser, such as a pipette or other suitable means. The sample is typically deposited onto the top of the zone 308. The sample addition zone 308 is capable of transporting the dispensed liquid sample from the point when the sample is deposited to a pair of parallel spaced reagent zones 312, 313 through an optional filter and adjacent reagent addition zone 315, preferably through capillary flow. The capillary flow inducing structure can include porous materials, such as nitrocellulose, or preferably through projections, such as micro-pillars or projections that can spontaneously induce capillary flow through the assay device 300, in the manner previously described. A filler material (not shown) can be also be placed within the sample addition zone 308 to filter particulates from the sample or to filter blood cells from blood so that plasma can travel through the assay device 300.

Located between the sample addition zone 308 and a detection zone 318 are a pair of adjacent reagent zones 312, 313, which are aligned in parallel relation herein. The reagent zones 312, 313 can include reagent(s) integrated into this analytical element and are generally reagents useful in the reaction—binding partners such as antibodies or antigens for immunoassays, substrates for enzyme assays, probes for molecular diagnostic assays, or are auxiliary materials such as materials that stabilize the integrated reagents, materials that suppress interfering reactions, and the like. Generally, one of the reagents useful in the reaction bears a detectable signal as discussed herein. In some cases, the reagents may react with the analyte directly or through a cascade of reactions to form a detectable signal such as a colored or fluorescent molecule. In one preferred embodiment, the reagent zones 312, 313 include conjugate material. The term "conjugate" means any moiety bearing both a detection element and a binding partner.

For purposes of this description, a detection element is an agent which is detectable with respect to its physical distribution and/or the intensity of the signal it delivers, such as but not limited to luminescent molecules (e.g., fluorescent agents, phosphorescent agents, chemiluminescent agents, bioluminescent agents and the like), colored molecules, molecules producing colors upon reaction, enzymes, radioisotopes, ligands exhibiting specific binding and the like. The detection element also referred to as a label is preferably chosen from chromophores, fluorophores, radioactive labels and enzymes. Suitable labels are available from commercial suppliers, providing a wide range of dyes for the labeling of antibodies, proteins and nucleic acids. There are, for example, fluorophores spanning practically the entire visible and infrared spectrum. Suitable fluorescent or phosphorescent labels include for instance, but are not limited to, fluoroceins, Cy3, Cy5 and the like. Suitable chemoluminescent labels include but are not limited to luminal, cyalume and the like.

Similarly, radioactive labels are commercially available, or detection elements can be synthesized so that they incorporate a radioactive label. Suitable radioactive labels include but are not limited to radioactive iodine and phosphorus; e.g., $^{125}I$ and $^{32}P$.

Suitable enzymatic labels include but are not limited to horseradish peroxidase, beta-galactosidase, luciferase, alkaline phosphatase and the like. Two labels are "distinguishable" when they can be individually detected and preferably quantified simultaneously, without significantly disturbing, interfering or quenching each other. Two or more labels may be used, for example, when multiple analytes or markers are being detected.

The binding partner is a material that can form a complex that can be used to determine the presence of or an amount of an analyte. For example, in a "sandwich" assay, the binding partner in the conjugate can form a complex including the analyte and the conjugate and that complex can further bind to another binding partner, also called a capture element, integrated into the detection zone. In a competitive immunoassay, the analyte will interfere with binding of the binding partner in the conjugate to another binding partner, also called a capture element, integrated into the detection zone. Example binding partners included in conjugates include antibodies, antigens, analyte or analyte-mimics, protein, etc.

Optionally located in the fluid flow path, before or after the reagent zone 312 and before the detection zone 318 is an optional reagent addition zone 315. The reagent addition zone 315 can allow the addition of a reagent externally from the device 300. For example, the reagent addition zone 315 may be used to add an interrupting reagent that can be used to wash the sample and other unbound components present in the fluid flow path into a wicking zone 324. In a preferred embodiment, the reagent addition zone 315 is located immediately downstream from the reagent zones 312, 313.

Still referring to FIG. 4 and downstream from the reagent zones 312, 313 and the optional reagent addition area 315 and along the lateral folded fluid path defined by the flow channel 317 is the detection zone 318, which is in fluid communication with the reagent zones. The detection zone 318 and/or the flow channel 317 may include a plurality of projections or micropillars, such as those as described above. Also as noted above, these projections are preferably integrally molded into the substrate from an optical plastic material such as Zeonor, such through an injection molding or embossing process. The width in the flow path in the detection zone 318 is typically on the order of about 0.5 mm-about 4 mm and preferably on the order of about 2 mm, although others can be prepared on the order of about 1 mm, provided sufficient signal for a suitable detection instrument, such as a fluorimeter, can be read even if the reagent plume does not cover the entire width of the detection zone.

The detection zone 318 is where any detectable signal can be read. In a preferred embodiment and attached to the projections in the detection zone 318 are capture elements. The capture elements can hold binding partners for the conjugate or complexes containing the conjugate, as described above. For example, if the analyte is a specific protein, the conjugate may be an antibody that will specifically bind that protein to a detection element such as fluorescence probe. The capture element could then be another antibody that also specifically binds to that protein. In another example, if the marker or analyte is DNA, the capture molecule can be, but is not limited to, synthetic oligonucleotides, analogues, thereof, or specific antibodies. Other suitable capture elements include antibodies, antibody fragments, aptamers, and nucleic acid sequences, specific for the analyte to be detected. A non-limiting example of a suitable capture element is a molecule that bears avidin functionality that would bind to a conjugate containing a biotin functionality. The detection zone 318 can include multiple detection zones. The multiple detection zones can be used assays that include one or more markers. In the event of multiple detection zones, the capture elements can include multiple capture elements, such as first and second capture elements. The conjugate can be pre-deposited on the assay device 300, such as by coating in the reagent zone. Similarly, the capture elements can be pre-deposited on the assay device on the detection zone 318. Preferably, both the detection and capture elements are pre-deposited on the assay device, or on the reaction zones 312, 313 and detection zone 318, respectively.

A brief treatment of the general process of the lateral flow assay device 300 will now be generally discussed. After a predetermined quantity of sample has been delivered to the sample addition zone 308, the sample will be caused to migrate laterally along the defined flow path into the parallel disposed pair of reagent zones 312, 313. The sample will continue to flow under capillary action according to this version of device and interact with the detection material impregnated within the projections of the reagent zones 312, 313. As the sample interacts, the detection material begins to dissolve in which a resultant detectable signal is contained within the fluid flow, which is subsequently carried into the adjacent reagent addition zone 315. Alternatively and in lieu of the reagent zones, 312, 313, the sample can be combined with the reagent having the detection material prior to adding to the sample addition zone 308. According to this version, the detection material includes the conjugate having both the detection element and binding partner, in which case it is often referred to as a conjugate plume and produces a fluorescent signal. Alternatively, the detectable signal can contain any of the reagent materials that have been dissolved in the reaction zone 312 or those added through the optional reagent addition zone 315.

Downstream from the detection zone 318 and along the folded fluid path is the wicking zone 324 in fluid communication with the detection zone 318. The wicking zone 324 is an area of the assay device 300 with the capacity of receiving liquid sample and any other material in the flow path, e.g. unbound reagents, wash fluids, etc. The wicking zone 324 provides a capillary force to continue moving the liquid sample through and out the intermediate detection zones of the assay device 300. The wicking zone 324 and other zones of the herein described device 300 can include a porous material such as nitrocellulose, or alternatively is a non-porous structure defined by projections as described previously. The wicking zone 314 can further include non-capillary fluid driving means, such as an evaporative heater or a pump. Further details of wicking zones as used in lateral flow assay devices according to the present invention are found in patent publications US 2005/0042766 and US 2006/0239859, both of which are incorporated herein by reference in their entireties.

According to at least one version, the entirety of the flow path of the assay device 300 including the sample addition zone 308, the reaction zones 312, 313, and the wicking zone 324 includes projections substantially vertical in relation to the substrate 304, and having a height, diameter and reciprocal spacing capable of creating lateral capillary flow of the sample in the flow path.

Components of the lateral flow assay devices (i.e., a physical structure of the device whether or not a discrete piece from other parts of the device) described herein can be prepared from copolymers, blends, laminates, metallized foils, metallized films or metals. Alternatively, device components can be prepared from copolymers, blends, laminates, metallized foils, metallized films or metals deposited one of the following materials: polyolefins, polyesters, styrene containing polymers, polycarbonate, acrylic polymers, chlorine containing polymers, acetal homopolymers and copolymers, cellulosics and their esters, cellulose nitrate, fluorine containing polymers, polyamides, polyimides, polymethylmethacrylates, sulfur containing polymers, polyurethanes, silicon containing polymers, glass, and ceramic materials. Alternatively, components of the device can be made with a plastic, elastomer, latex, silicon chip, or metal; the elastomer can comprise polyethylene, polypropylene, polystyrene, polyacrylates, silicon elastomers, or latex. Alternatively, components of the device can be prepared from latex, polystyrene latex or hydrophobic polymers; the hydrophobic polymer can comprise polypropylene, polyethylene, or polyester. Alternatively, components of the device can comprise TEFLON®, polystyrene, polyacrylate, or polycarbonate. Alternatively, device components are made from plastics which are capable of being embossed, milled or injection molded or from surfaces of copper, silver and gold films upon which may be adsorbed various long chain alkanethiols. The structures of plastic which are capable of being milled or injection molded can comprise a polystyrene, a polycarbonate, or a polyacrylate. In a particularly preferred embodiment, the lateral flow assay devices are injection molded from a cyclo olefin polymer, such as those sold under the name Zeonor®. Preferred injection molding techniques are described in U.S. Pat. Nos. 6,372,542, 6,733, 682, 6,811,736, 6,884,370, and 6,733,682, all of which are incorporated herein by reference in their entireties.

The defined flow path of the lateral flow assay devices described herein, including device 300, can include open or closed paths, grooves, and capillaries. Preferably, the flow path comprises a lateral flow path of adjacent projections, having a size, shape and mutual spacing such that capillary flow is sustained through the flow path. In one embodiment, the flow path is in a channel within the substrate 304 having a bottom surface and side walls. In this embodiment, the projections protrude from the bottom surface of the flow channel. The side walls may or may not contribute to the capillary action of the liquid. If the sidewalls do not contribute to the capillary action of the liquid, then a gap can be provided between the outermost projections and the sidewalls to keep the liquid contained in the flow path defined by the projections. Preferably, the reagent that is used in the reaction zones 312, 313 and the capture members or detection agent used in the detection zone 318 is bound directly to the exterior surface of the projections used in the herein described assay device 300.

Tests (assays) are typically completed when the last of the conjugate material has moved into the wicking area 324 of the lateral flow assay device 300. At this stage, a detection instrument, such as a fluorimeter or similar device, is used to scan the detection zone 318, the detection instrument being movable and aligned optically with the flow channel 317 along an axis 319. The detection instrument that can be used to perform the various methods and techniques described herein can assume a varied number of forms. For example and as described according to the present embodiment, the instrument can be a scanning apparatus that is capable of detecting fluorescence or fluorescent signals. Alternatively, an imaging apparatus and image analysis can also be used to determine, for example, the presence and position of at least one fluorescent fluid front of an assay device. According to yet another alternative version, infrared (IR) sensors could also be utilized to track the position of fluid position in the lateral flow assay device. For instance, an IR sensor could be used to sense the ~1200 nanometer peak that is typically associated with water in the fluid sample to verify that sample had indeed touched off onto the substrate of the assay device. It should be readily apparent that other suitable approaches and apparatus capable of performing these techniques could be utilized herein.

For purposes of this embodiment, the detection instrument is incorporated within a portable (hand-held or bench top) testing apparatus that includes means for receiving at least one lateral flow assay device 300 and defining a scan path along the flow channel 317 and coincident with axis 319 relative to a light emitting element of the detection instrument, such as a laser diode and an optical system and filtering, having an optical axis and capable of providing quantitative measurement of fluorescent signal at predefined wavelengths as emitted from the assay fluorophores in the lateral flow assay device, and as discussed herein. Other devices or testing apparatus can also be used to retain a detection instrument for purposes of the herein described monitoring methods. For example, a mainframe clinical analyzer can be used to retain a plurality of lateral flow assay devices as described in copending U.S. Ser. No. 61/658,698, filed Jun. 12, 2012, the entire contents of which are herein incorporated by reference. In a clinical analyzer at least one detection instrument, such as a fluorimeter, can be aligned with the flow channel of the device and provided, for example, in relation to an incubator assembly as a monitoring station in which results can be transmitted to a contained processor.

One exemplary flow monitoring methodology is now herein described. For purposes of this method and in the description that follows, a lateral flow assay device as previously described according to FIG. 4 is utilized, although other device configurations could be utilized, this embodiment intended to be exemplary of a more generic technique.

For purposes of this particular version, a pair of detection or reader apparatuses are employed; namely, a first reader apparatus 331 that is linearly aligned with the linear section of flow channel 317 containing the detection zones 318 along axis 319 and a second reader apparatus 334 that is linearly aligned with the wicking zone 324 along a second axis 337. In each of the foregoing apparatus, a reader or detector such as fluorimeter can be translated along the respective axes 319, 337 relative to specific areas designated on the lateral flow assay device 300. Alternatively, a single reader apparatus (not shown) could be utilized, the reader apparatus having capability of translating longitudinally and laterally so as to selectively align with either detection axis 319 or 337.

Before sample is administered or otherwise dispensed, the lateral flow assay device 300 can first be assessed by performing a so-called "dry scan" or read using each of the first and second reader apparatus 331, 334 at specific areas of the lateral flow assay device 300. For purposes of this embodiment, readings are taken at using the second reader apparatus 334 adjacent the entrance and exit of the wicking zone 324 at designated positions 351 and 355, respectively, and the first reader apparatus 331 takes a reading at the detection zone 318. The purpose of the "dry scan" is to obtain a background signal level prior to dispensing sample and comparing the background signal to a known standard. Readings that exceed the background standard can be indicative of error conditions, such as device structural flaws or a premature leakage of reagent or previous use. In any event, determinations that are not within a suitable range of the background signal can be detected by either reader apparatus and cause the assay device 300 to be discarded.

Alternatively, or in addition to, immediately upon installation of the device into the testing apparatus and either before or after addition of sample to the device 300, readings are taken at the wicking zone, such as at the exit of the wicking zone 324, at a designated position 355. Readings that exceed the background standard can be indicative of error conditions, such as premature leakage of reagent or evidence of previous use. In any event, determinations that are not within a suitable range of the background signal can be detected and cause the assay device 300 to be discarded.

Sample is dispensed onto the sample addition zone of the assay device 300 which is loaded into a testing apparatus (not shown), such as a clinical analyzer, a desk-top or point of care device. Sample can be administered upon installing the assay device 300 into the testing apparatus or following its installation. The testing apparatus according to this exemplary embodiment includes a processor (not shown) having timing means and sufficient memory. A timer is initiated from the time sample is dispensed or when a device is loaded within the testing apparatus that causes sample to be dispensed. The first reader apparatus 331 remains aligned with the detection zone 318 for the initial detection of the detectable signal produced in this instance by the conjugate plume caused by the dissolution of the detection material as this material interacts with the flowing sample. According to the method, the reader apparatus 331 is configured to periodically conduct readings (e.g., each 1.5-2.5 seconds) following the administration of sample until the presence of the conjugate front is initially detected by means of a large increase in signal by the reader apparatus 331. The time ($T_a$) elapsing from the dispense of sample until this signal is detected is compared to a predetermined standard time interval ($T_0$) and is recorded into the attendant memory of the testing apparatus. If $T_a$ is greater than the predetermined standard time interval $T_0$, further testing of the device can be terminated as this is indicative of either device and/or process issues. An error message or signal can also be forwarded to the user of the apparatus, either audibly or by other suitable means.

Figure 5:
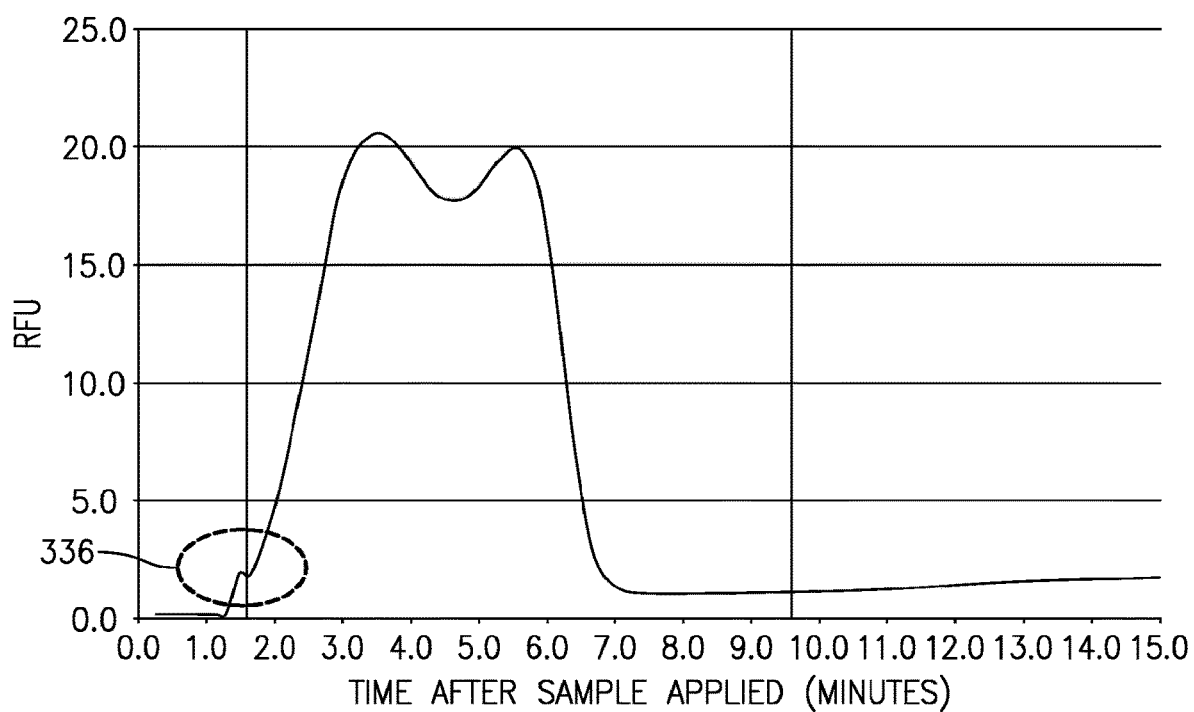
FIG. 5 is a graphical representation of a stepped output of a detection signal and more specifically an output involving a fluorescent or conjugate plume of a lateral flow assay device having a plurality of reaction zones.

Following the determination of $T_a$, the first reader apparatus 331 can continue according to this embodiment to monitor the detection zone 318 at predetermined intervals (e.g., about 2 seconds) over a predetermined time period (e.g., 10 seconds) in order to obtain a signal profile relating to the reagent zone(s). Errors can be detected through comparison to a standard profile or otherwise that is stored by the testing apparatus. For example and referring to FIG. 5 for an assay devices configured with multiple (N) reagent zones 312, 313 a total of N fluorescent signals (plumes) would be generated in the flow channel of the device within a certain time frame. If one or more of the resulting plumes is delayed (e.g., slow flow through the passageway), then the fluorescent signal will feature distinct steps in its rise. If these steps occur over a time frame that is greater than a predetermined threshold, then there may be a reason to believe dissolution of the conjugate material is not occurring normally, resulting in an error. As depicted in FIG. 5, such a step is shown as indicated by the circled region 336, and indicative of potential delays between the parallel disposed reagent zones 312, 313.

The conjugate front (the front of the liquid sample containing the detectable signal as dissolved from the reagent zones 312, 313) can then be further detected in relation to the wicking zone 324 of the assay device 300. Using the second reader apparatus 334 according to this embodiment, the reader is moved to the position 351 adjacent to the entrance of the wicking zone 324. Still utilizing the initial timer and processor that has stored the time in which sample was dispensed and $T_a$, the second reader apparatus 334 is configured to read at predetermined intervals (e.g., 1 second) until the signal indicative of the presence of the conjugate front is detected in the same manner, as previously discussed. The time in which the front is detected is stored by the processor and compared to a standard time interval that is also stored within the processor, as measured from either $T_a$ or based upon the time sample was first dispensed. If this comparison is not suitable; that is, if the time taken exceeds the stored standard time interval, then the test may be terminated and the device 300 may be discarded.

The time taken for the conjugate front to reach the entrance 351 of the wicking zone 324 as detected by the second reader apparatus is also recorded by the processor. In addition to determining whether the device 300 is performing properly prior to analyte measurement at the conclusion of the test, the detection of the conjugate front and the detectable signal can further be utilized to control other process-related events. For example, it is known that wash fluid can be added after all of the sample has been dispensed and has moved through the assay device 300 to the wicking zone 324. Using the present method, this determination can be made qualitatively by determining when all of the conjugate material in the reagent zones 312, 313 has dissolved. In one version, the first reader apparatus 331 can be moved to the detection zone 318 following the detection of conjugate at the entrance of the wicking zone 324. Readings can be taken at predetermined intervals until the termination of signal; see, FIG. 5. The time taken ($T_e$) for the termination of signal is indicative of the end of the conjugate material, which can be compared to a stored standard value. If $T_e$ is excessive, the test may be terminated and the device 300 may be discarded.

According to this version and if $T_e$ is within the predetermined standard, then wash reagent can be added to the optional reagent addition zone 315. Alternatively, it has been determined that the fluid volume in the wicking zone 324 can be used to trigger wash reagent addition. According to this version, the second reader apparatus 334 is initially positioned, for example and according to this exemplary embodiment along the span of the wicking zone 324 between the entrance and exit ends thereof, for example, at about the center thereof at position 353. The reader apparatus 334 is then configured to make readings at predetermined time intervals (e.g., 1 second) until a signal rise indicative of the presence of the conjugate fluid front is detected. The time for the arrival of the conjugate front ($T_{wzcenter}$) is compared to a predetermined standard time interval. If $T_{wzcenter}$ is greater than the stored predetermined value, then the test may be terminated and the device 300 may be discarded. If this time is within acceptable limits, then the dispense of wash fluid can be initiated from zone 515 to flush the unbound material to the wicking zone 324.

Additional quality assurance can be provided according to this embodiment after a wash step has been initiated. For example and once $T_{wzcenter}$ has been determined, a first flow rate can be determined by the relation $Q_1=V_1/(T_{wzcenter}-T_{wzentrance})$ in which $V_1$ is the fluid volume inside the wicking zone and $T_{wzcenter}$ and $T_{wzentrance}$ are equal to the time in which the liquid front was initially detected at the interior of the wicking zone 353 and the entrance 351 of the wicking zone 324, respectively. The wicking zone fluid volume $V_1$ is known from the dimensions of the assay device design and is previously stored by the processor of the testing apparatus. The second reader apparatus 334 is then moved to the exit end 355 of the wicking zone 324 and readings are taken at predetermined intervals (e.g., 1 second) until a signal is detected indicative of the presence of the conjugate front initially reaching the exit end 355. The time taken to obtain this reading, as compared to either the time sample was dispensed initially or alternatively $T_a$ is determined and compared to a stored predetermined standard. If this time ($T_{wzexit}$) is greater than the predetermined standard, then the test is terminated and the assay device 300 may be discarded.

Assuming the detected time to the exit end 355 of the wicking zone 324 is acceptable, the time ($T_{wzexit}$) is recorded and a second fluid flow rate is calculated between the center 353 of the wicking zone and the exit end 355 of the wicking zone 324, as follows: $Q_2=V_2(T_{wzexit}-T_{wzcenter})$ in which $V_2=V_0-V_1$ ... in which both $V_0$ and $V_1$ are each known values that are previously stored by the processor of the testing apparatus. The ratio of the calculated flow rates within the wicking zone 324, $Q_2/Q_1$ is then calculated and compared to a stored threshold.

The prior discussion utilized a pair of readers to make signal/time determinations regarding the detection of the signal front. Alternatively and referring to FIG. 6, a single reader can be provided relative to each of the detection or scan paths (axes 319, 337) in which the reader is configured for movement in two horizontal planar dimensions. According to yet another version, a single reader can also be provided relative to the axis 319. More specifically, the lateral flow assay device can be reconfigured such that at least one capillary channel can extend, for example, from one or more points in the wicking zone 324 past a position aligned along the preferably linear scan path 319 of the device to permit monitoring by the reader apparatus.

Figure 6:
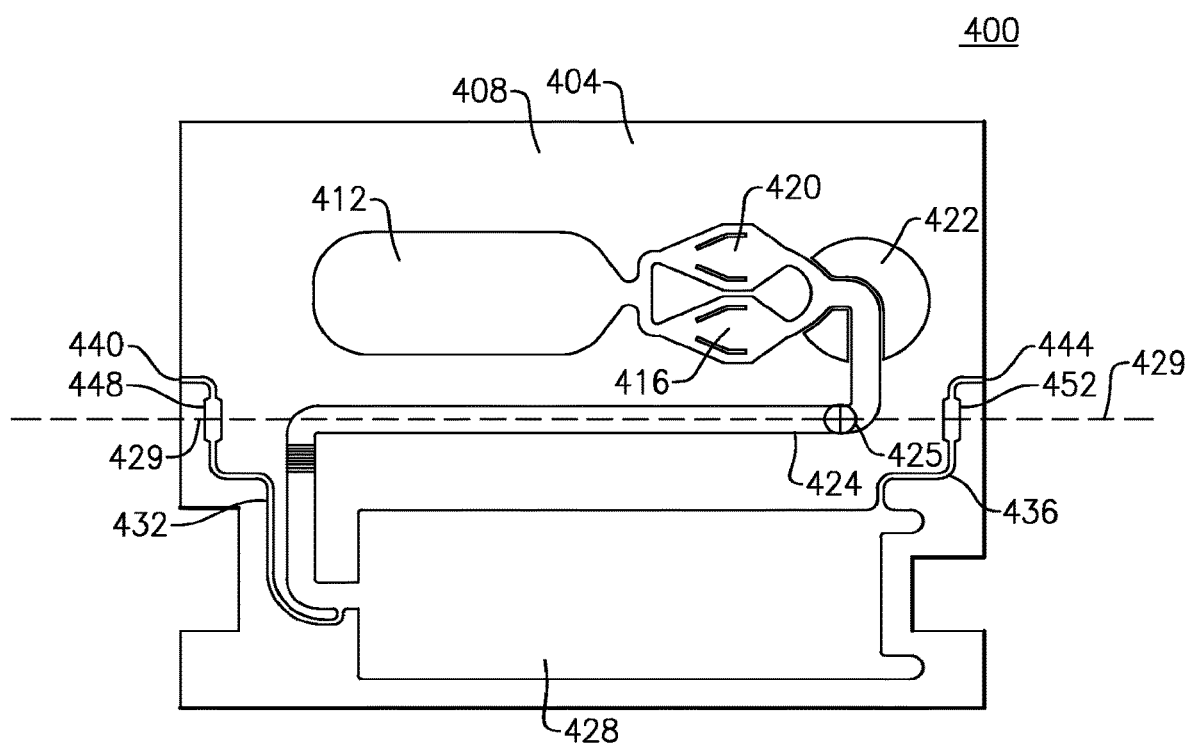
FIG. 6 is a top plan view of an exemplary lateral flow assay device design that includes diverting channels extending between the wicking zone and the linear detection portion of the device, the device also being useful for the methods described herein.

An exemplary version of an assay device 400 that is configured with at least one capillary channel is depicted at FIG. 6. This assay device 400 is defined by a planar substrate 404 manufactured from a non-porous material, such as a moldable plastic, although porous materials could alternatively be utilized. The substrate 404 is defined by a top or upper surface 408 further defined by a plurality of discrete areas or zones including a sample receiving area 412 that is fluidly interconnected to a pair of parallel reagent zones 416, 420, each of the latter zones including a detection material deposited therein, preferably to a plurality of projections that promotes capillary flow and interacts with a liquid sample as discussed previously, the reagent zones being fluidly interconnected within a flow channel 424 extending as a folded fluid flow path of the device 400 that includes at least one detection zone or area 425 and further extending to a downstream receiving or wicking zone 428. A linear portion of the flow channel 424, defines a detection portion (scan path) as represented by dotted axis 429, which can be aligned with a suitable detection instrument, such as a fluorimeter (not shown). As in the preceding, an optional reagent addition zone 422, such as a wash zone, is also provided adjacent the reaction zones 416, 420.

Still referring to FIG. 6 and according to this embodiment, a pair of microchannels 432, 436 are provided interconnecting the wicking zone 428 of the device with the flow channel 424 and more specifically the detection portion 429 of the device 400. More specifically, a first microchannel 432 is connected at one end to the flow channel 424 at or near the entrance of the wicking zone 428 while the second microchannel 436 extends substantially from the end or exit of the wicking zone. Each of the microchannels 432, 436 extend through the detection axis 429 to lateral sides of the substrate 404 and are defined with respective vents 440, 444, exposing same to ambient air. Each of the first and second microchannels 432, 436 are defined with widths of about 0.05 mm to about 0.1 mm and include expanded portions 448, 452 which according to this embodiment have a length of about 1.1 mm and a width no larger than 0.5 mm, each of the expanded portions creating a read window for purposes of a detection instrument and in which each of the expanded portions 448, 452 are aligned with each other as well as the linear flow channel 224 along the defined detection axis 429.

Additional monitoring locations can be provided for purposes of this design, for example, providing at least one further microchannel (not shown), for example extending from substantially the center of the wicking zone 428 and in which the microchannel includes an expanded portion (read window) that is aligned along the detection portion 429. A vent can be provided for the latter microchannel at the lateral edge of the device substrate 404 or alternatively an opening can be formed in a hydrophilic cover (not shown) of the wicking zone 428. Preferably, any microchannels are as small as possible and in which the width of the channel is no greater than about 30 microns at the bottom of the channel. In addition and in at least one embodiment, an estimate of the flow velocity or fluid flow rate can be calculated from the time the conjugate plume appears at any two points within the wicking zone over a known distance. The time 344 between detection of signal can be used to calculate fluid flow rate over the known distance between the microchannels. According to at least one version, the flow velocity or a measured time of the sample can then be utilized for providing post prediction corrections. Additional methodology is described in U.S. patent application Ser. No. 14/081,158, entitled: Calibrating Assays Using Reaction Time, first named inventor: Zhong Ding, filed concurrently herewith, the entire contents of which are herein incorporated by reference.

The basic operational principles of this assay device 400 are similar to those previously described. That is, a quantity of a sample is applied to the sample receiving area 412, which is transmitted by capillary force under the influence of the projections defining same to the reagent zones 416, 420. In each of the reagent zones 416, 420, bound detection material is dissolved and a detectable signal, such as a fluorescent conjugate plume, is created proximate the moving front of the fluid sample. In the case of multiple reagent areas, as in this device design, the creation of the detectable signal could be delayed, thereby producing a stepped output in which an initial detectable signal is present followed at a later or somewhat contemporaneous portion of the flowing sample by another signal or a signal of increased intensity.

The sample continues to move through the detection zone(s) 425 of the device 400 until the fluid reaches the entrance of the wicking zone 428 at which a portion of the sample is drawn off into the microchannel 432. This diverted fluid portion is moved under capillary action past the expanded portion 448 that is aligned with the detection portion 429 so as to be identified by the detection instrument. The time at which this latter signal is indicative of the fluid entering the wicking zone 428. To that end, fluid sample, unbound material and/or wash fluid is caused to be moved under capillary force through the wicking zone 428 under the influence of the projections and/or hydrophilic cover (not shown) according to this embodiment. As sample and unbound detection material is progressed to the end of the wicking zone 428, another portion is siphoned into the microchannel 436 under capillary action and moved past the defined read window 452 which is also aligned with detection axis 429 for identification of same by the detection instrument. Understanding the time between the detection of signals indicative of the presence of material at the entrance and exit of the wicking zone 428 as well as knowing the distance between the microchannels 432, 436 enables one to determine flow rate of the sample, as well as other related flow-related process parameters.

According to yet another aspect and due to the nature of the fluorescent conjugate detection material discussed herein, it is also possible to detect the presence of unconjugated or free detection material in specific areas of the lateral flow assay device. These areas can be identified in accordance with the methods previously described using the scanning apparatus to detect for same along the flow channel. Alternatively and in the instance in which the wicking zone is not part of the fluid flow path, at least one capillary channel can be branched out from the wicking zone of a lateral flow assay device at the point of interest and brought up to the flow path where the presence of this material could be scanned for using the scanning apparatus as previously discussed referring to FIG. 6. During deposition, a droplet of unconjugated fluorophore could be spotted in the capillary just beyond the junction where the capillary joins the wicking zone. This unconjugated material would be easily dissolved by the fluid entering the capillary and would provide a robust signal when the fluid arrives at the end of the capillary (which is within the scan path of the device). Similarly, if it was important to track the location of the fluid front as it progresses along the flow channel, a very small amount of unconjugated fluorophore could be deposited at the entrance of the flow channel in that conjugate material has not had adequate time to dissolve in this initial front of fluid.

EXAMPLES

Example 1

Plastic substrate chips made of Zeonor (Zeon, Japan) having oxidized dextran on the surface for covalently immobilization of proteins via Schiff base coupling were used. Fluorescently labeled Anti-NT-proBNP monoclonal antibody was deposited and dried to create a reagent zone. Anti-NT-proBNP monoclonal antibody was deposited and dried to create a detection zone. A small amount of Triton X-45 was deposited on the device to increase wettability of the sample for better capillary flow. The signal intensities from the fluorescently labeled complexes in the detection zone were recorded in a prototype line-illuminating fluorescence scanner. Referring to FIG. 5, for an assay device configured with multiple (N) reagent zones, a total of N fluorescent signals (plumes) would be generated in the flow channel of the device within a certain time frame. If one or more of the resulting plumes is delayed (e.g., slow flow through the passageway), then the fluorescent signal will feature distinct steps in its rise. If these steps occur over a time frame that is greater than a predetermined threshold, then there may be a reason to believe dissolution of the conjugate material is not occurring normally, resulting in an error. As depicted in FIG. 5, such a step is shown as indicated by the circled region 336, and indicative of potential delays between the multiple reagent zones.

Example 2

Figure 7:
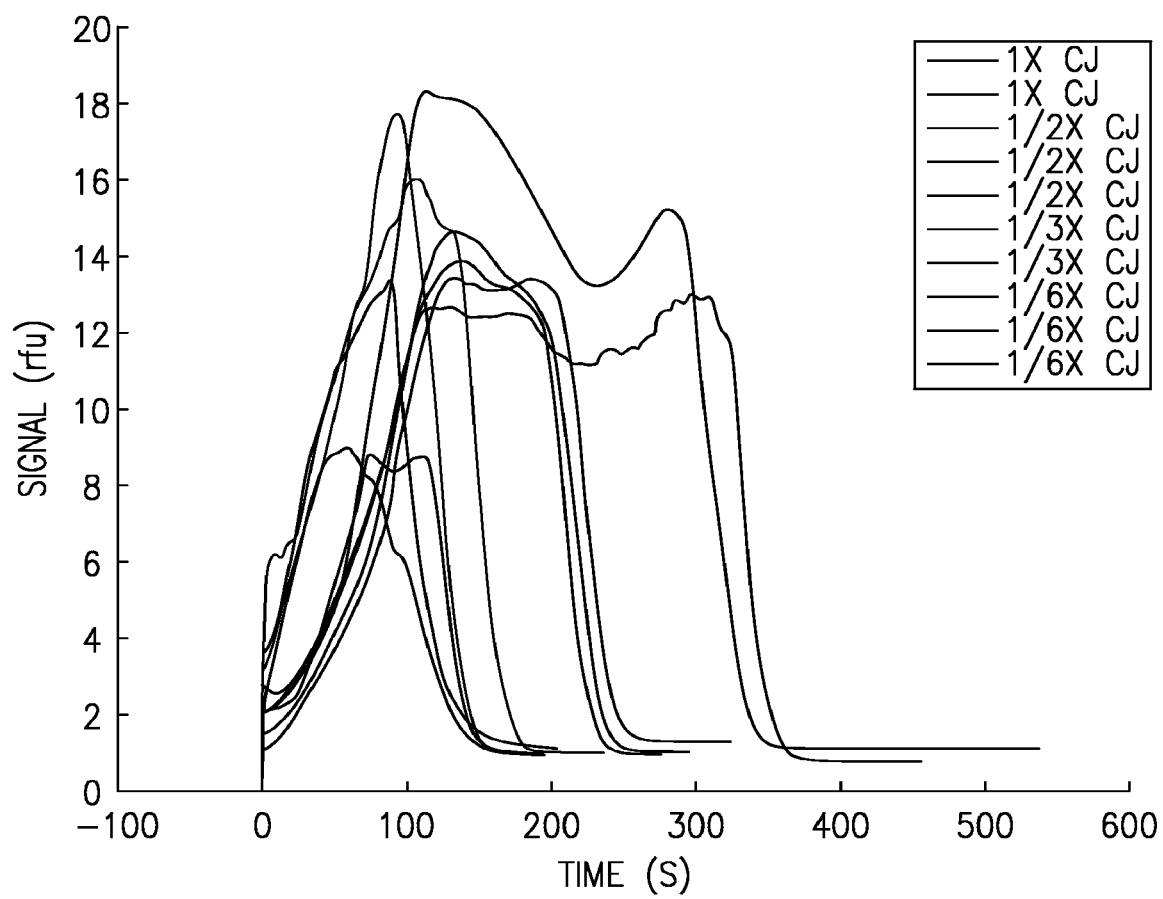
FIG. 7 is a graphical depiction comparing various detection signal profiles based on dissolution of different deposition amounts and patterns of detection material on an assay device over time.

If the end of the fluorescent plume is not detected prior to a predetermined time interval as detected by the scanner, this could indicate an anomaly, including i) an excessively fast fluid flow rate; ii) too little conjugate material being initially present on the chip; or iii) another defect in the reagent zone that caused the material to dissolve too quickly. In this example, assay devices were prepared in a similar manner as Example 1, all using the same chip design. Referring to FIG. 7, different deposition patterns and amounts provided in the reagent zones on multiple assay devices varying between 1× and ⅙× of the Anti-NT-proBNP monoclonal antibody conjugate material and based on differing sample viscosities. As shown in FIG. 7, the amount of detection material directly affects the shape of the resulting profiles, as well as the maximum signal detected and the overall time duration of each profile. The appearance of the plume at various milestone points along the flow channel as well as the signal level and duration can be ascertained and therefore determine in accordance with the herein described method, differences between a viscous sample and a flow issue.

Example 3

Figure 8:
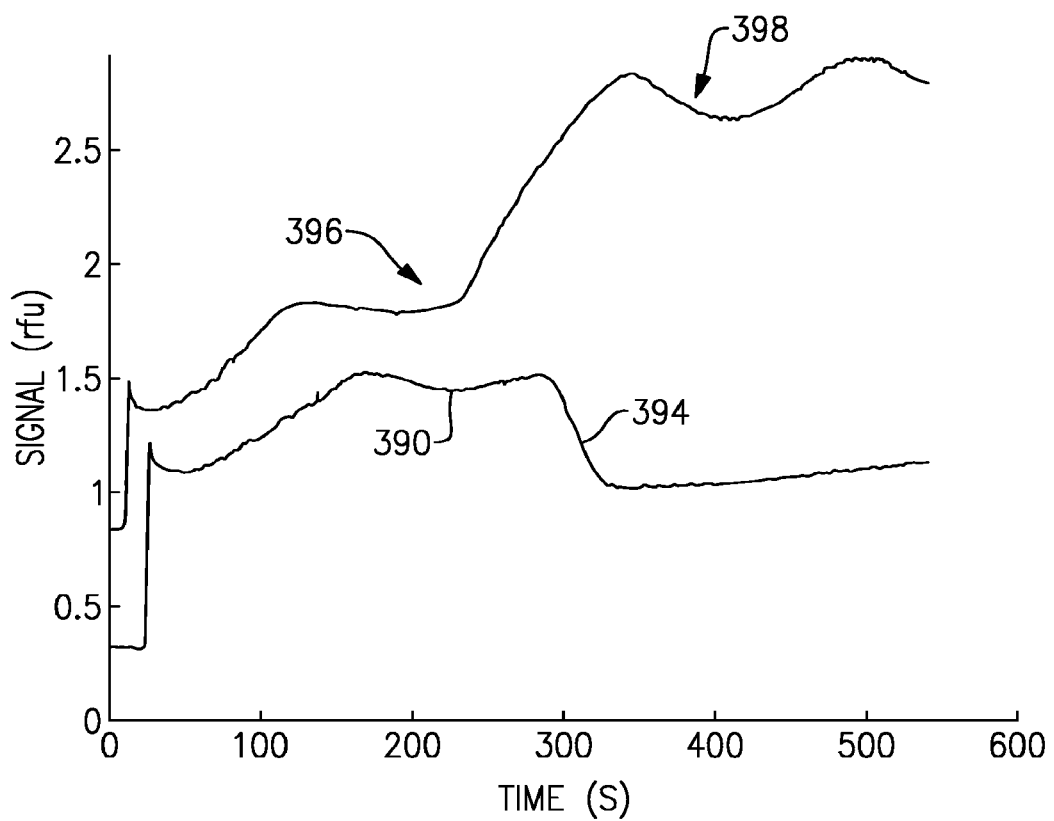
FIG. 8 is a comparative graphical depiction of various detection signal profiles on an assay device.

Assay devices were again prepared in a similar manner as Example 1, all using the same chip design. In this example and referring to FIG. 8, an exemplary detection signal profile 390 that clearly depicts a portion 394 of the profile that returns to a base or background level is contrasted with a separate profile 396 including a portion 398 thereof indicative of stopped flow. The failure to detect the end of the fluorescent signal at all after a maximum elapsed time interval, could be indicative of certain anomalies, such as: i)

an excessively slow fluid flow rate (or lack of flow rate entirely); ii) an inadequate sample volume; iii) excessive conjugate (detection) material initially present on the assay device or added with sample to the sample addition zone; or iv) another defect in the reagent zone or flow channel that caused the detection material to dissolve too slowly.

PARTS LIST FOR FIGS. 1-8

1 assay device
2 sample addition area or zone
3 reagent zone or area
4 detection area or zone
5 wicking area or zone
7 projections
20 lateral flow assay device
40 substrate
44 top surface
48 sample receiving area or zone
52 reaction area or zone
56 detection area(s) or zone
60 wicking area or zone
64 flow channel
68 plurality of projections
70 hydrophilic layer
72 vent areas
100 lateral flow assay device
104 substrate
108 sample addition (receiving) area
112 reagent (reaction) zone or area
114 detection area or zone
116 flow channel
120 wicking (receiving) zone or area
124 reagent addition zone
130 projections
300 lateral flow assay device
304 substrate, planar
308 sample addition (receiving) zone or area
312 reagent (reaction) zones or areas
315 reagent addition zone (optional)
317 flow channel
318 detection zone or area
319 axis
324 wicking (receiving) zone or area
331 first reader apparatus
334 second reader apparatus
336 circled region
337 axis
351 detection position, entrance end, wicking zone
353 detection position, center, wicking zone
355 detection position, exit end, wicking zone
390 profile
394 portion, profile
396 profile
398 portion, profile
400 lateral flow assay device
404 substrate, planar
408 top or upper surface
412 sample addition area
416 reagent area or zone
420 reagent area or zone
422 reagent addition area
424 flow channel
425 detection area or zone
428 wicking area or zone
429 detection portion
432 microchannel
436 microchannel
440 vent
444 vent
448 expanded portion (read window)
452 expanded portion (read window)

It will be readily apparent that other modifications and variations are possible within the intended ambits of the concepts described herein and in accordance with the following claims.

The invention claimed is:

1. A method for processing a lateral flow assay device, the lateral flow assay device comprising a substrate having at least one sample addition zone, a first detection zone downstream of the at least one sample addition zone, at least one wash zone down stream of the at least one sample addition zone and up stream of the first detection zone, and at least one wicking zone disposed downstream of the first detection zone wherein the at least one wicking zone includes a second detection zone, each of the zones being fluidly connected along a flow path in which a sample flows from the at least one sample addition zone to the at least one wicking zone, said method comprising the steps of:
adding a quantity of a sample to the at least one sample addition zone of the lateral flow assay device;
combining the sample and a reagent, wherein the sample and reagent may be combined prior to the adding of the sample to the at least one sample addition zone or on the assay device, the reagent including a detection material that produces a detectable signal that flows through the remainder of the lateral flow assay device along the flow path; and
triggering a process-related wash event including a dispense of at least one wash fluid into the at least one wash zone based upon the detection of the detectable signal in at least the first detection zone and a second signal at the second detection zone.

2. A method as recited in claim 1, wherein the reagent, including the detection material, is disposed in at least one reagent zone disposed downstream of the at least one sample addition zone and fluidly connected therewith.

3. A method as recited in claim 2, including the additional steps of:
monitoring the first detection zone, the second detection zone, or a combination thereof;
determining the time sample carrying the detectable signal is initially detected in the first detection zone, the second detection zone, or a combination thereof;
comparing the determined time to a known time period; and
triggering the process-related event upon the lateral flow assay device only if said determined time is within a threshold of the known time period.

4. A method as recited in claim 1, wherein the dispense of at least one wash fluid onto the wash zone is to flush out sample and detection material.

5. A method as recited in claim 1, wherein the second detection zone is at an initiation of the at least one wicking zone of the lateral flow assay device.

6. A method as recited in claim 1, further comprising the step of providing at least one capillary channel for diverting a portion of sample from the flow path across a linear detection path of the lateral flow assay device extending through the at least one detection zone; and
detecting the presence or lack of presence of the detectable signal in the channel, the detecting step causing the triggering of the process-related event.

7. A method as recited in claim 1, wherein the detection material is a conjugate material that produces a fluorescent plume.

8. A method as recited in claim 1, wherein the lateral flow assay device includes a plurality of projections disposed on the at least one wicking zone, the plurality of projections being dimensioned to induce capillary flow along the flow path.

9. A method as recited in claim 2, including the additional step of monitoring at least one predetermined zone of the lateral flow assay device for the presence of detection material in any zone outside of the at least one reagent zone and prior to application of sample to the at least one sample addition zone.

10. A method as recited in claim 2, including the additional step of calculating at least one flow related parameter based on the monitoring of at least one of the appearance and cessation of the detectable signal at the first detection zone, the second detection zone, or a combination thereof.

11. A method as recited in claim 2, including the additional step of determining the cessation of the detectable signal at the first detection zone, the second detection zone, or a combination thereof.

12. A method as recited in claim 3, wherein the monitoring step is performed in the second detection zone.

13. A method as recited in claim 2, including the additional step of monitoring the first detection zone, the second detection zone, or a combination thereof and determining the amount of dissolved detection material in the at least one monitored area over a time period.

14. A method as recited in claim 2, including the additional step of monitoring the first detection zone, the second detection zone, or a combination thereof from the appearance to the termination of the detectable signal.

15. A method as recited in claim 14, including the additional step of creating a time history of the detectable signal relating to the at least one monitored area of the lateral flow assay device.

16. A method as recited in claim 1, wherein the dispense of wash fluid includes dispense of a reagent.

17. A method as recited in claim 1, wherein the second signal is the presence of a conjugate front.

* * * * *